United States Patent
Maguire et al.

(10) Patent No.: US 10,209,241 B2
(45) Date of Patent: Feb. 19, 2019

(54) HIGH THROUGHPUT SENSITIZATION DETECTION DEVICES AND METHODS

(75) Inventors: Tim Maguire, Piscataway, NJ (US); Martin L. Yarmush, Newton, MA (US); Rene S. Schloss, East Brunswick, NJ (US); Bhaskar Mitra, Pradesh (IN); Rohit Jindal, Braintree, MA (US); Mehdi Ghodbane, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1386 days.

(21) Appl. No.: 14/238,624

(22) PCT Filed: Aug. 10, 2012

(86) PCT No.: PCT/US2012/050375
§ 371 (c)(1),
(2), (4) Date: Jul. 25, 2014

(87) PCT Pub. No.: WO2013/025519
PCT Pub. Date: Feb. 21, 2013

(65) Prior Publication Data
US 2014/0336078 A1    Nov. 13, 2014

Related U.S. Application Data

(60) Provisional application No. 61/522,787, filed on Aug. 12, 2011.

(51) Int. Cl.
*C12M 3/00*         (2006.01)
*G01N 33/50*        (2006.01)
(Continued)

(52) U.S. Cl.
CPC .... *G01N 33/5023* (2013.01); *B01L 3/502761* (2013.01); *G01N 33/5047* (2013.01); *G01N 33/5082* (2013.01); *G01N 33/54366* (2013.01); *G01N 33/6863* (2013.01); *B01L 2200/0668* (2013.01); *B01L 2300/0877* (2013.01);
(Continued)

(58) Field of Classification Search
CPC ...... C12M 23/16; C12M 25/02; C12M 25/04; C12M 25/14; G01N 33/5064
See application file for complete search history.

(56) References Cited

U.S. PATENT DOCUMENTS 5,496,697 A * 3/1996 Parce ............... C12M 23/12
                                               435/29
5,591,636 A * 1/1997 Grass ............... B01D 61/18
                                               324/450
(Continued)

FOREIGN PATENT DOCUMENTS

WO    2005100995    10/2005

*Primary Examiner* — William H. Beisner
(74) *Attorney, Agent, or Firm* — Fox Rothschild LLP

(57) ABSTRACT

This invention discloses devices and methods for high throughput skin sensitization detection. The devices comprise a microfabricated chamber comprising a region having one or more input channels and an outlet, and a face suitable for mounting a skin tissue and in fluidic communication with the region. The devices can be used in the methods for determining a prognosis of sensitization in an animal subject and identifying compounds that do not cause sensitization and thus are suitable for preparing cosmetic compositions.

37 Claims, 6 Drawing Sheets

(51) Int. Cl.
  *G01N 33/543* (2006.01)
  *G01N 33/68* (2006.01)
  *B01L 3/00* (2006.01)
  *C12M 3/06* (2006.01)

(52) U.S. Cl.
  CPC ........ *B01L 2400/086* (2013.01); *C12M 23/16* (2013.01); *G01N 33/5064* (2013.01); *G01N 2333/7051* (2013.01); *G01N 2333/70596* (2013.01); *G01N 2333/7151* (2013.01); *G01N 2333/7155* (2013.01); *G01N 2500/10* (2013.01)

(56) References Cited

U.S. PATENT DOCUMENTS

| | | |
|---|---|---|
| 6,900,021 B1 | 5/2005 | Harrison et al. |
| 7,935,522 B2 * | 5/2011 | Thomas ................ B01L 3/5027 422/72 |
| 2002/0022789 A1 | 2/2002 | Perez et al. |
| 2010/0137153 A1 | 6/2010 | Link et al. |
| 2011/0125058 A1 | 5/2011 | Levinson et al. |

* cited by examiner

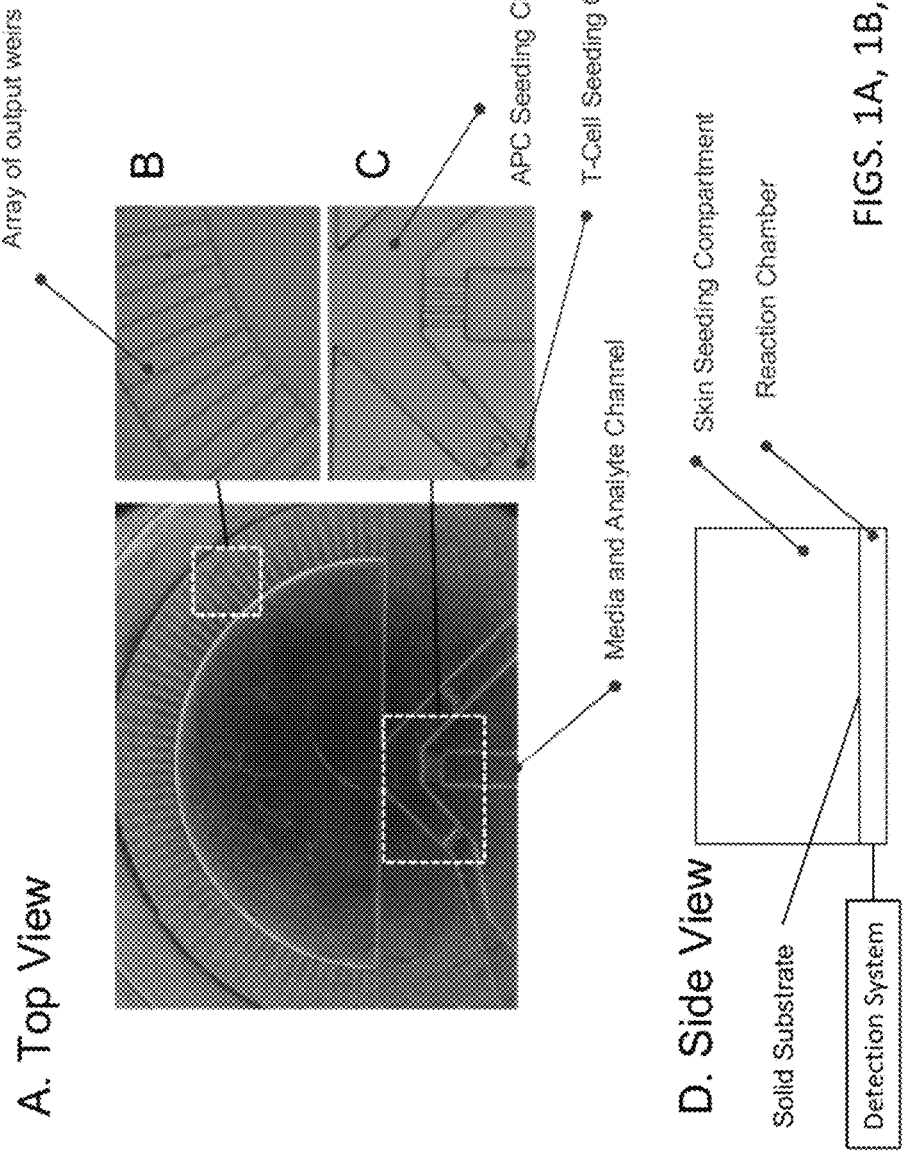
FIGS. 1A, 1B, 1C, and 1D

HIGH THROUGHPUT SENSITIZATION DETECTION DEVICES AND METHODS

CROSS REFERENCE TO RELATED APPLICATIONS

This application is a U.S. National Phase of International Application PCT/US2012/050375, filed Aug. 10, 2012, which claims the benefit under 35 U.S.C. § 119(e) of U.S. Provisional Application No. 61/522,787, filed on Aug. 12, 2011. The disclosures of both applications are incorporated herein by reference in their entirety.

FIELD OF THE INVENTION

This invention relates to devices and methods for detection of skin sensitization, especially determining skin-sensitizing or non-sensitizing property of agents in a parallel or high throughput manner.

BACKGROUND OF THE INVENTION

Skin sensitization is a skin response to an allergen. It results in allergic contact dermatitis and is a common occupational and environmental health issue. Indeed, allergic contact dermatitis is the most common manifestation of immuno-toxicity in humans. Allergic contact dermatitis is not life-threatening, but can be associated with considerable morbidity. Various chemicals have been implicated as skin sensitizers. Traditionally, guinea pigs were used for identification of chemicals or other agents that cause skin sensitization. Recently, a murine local lymph node assay (LLNA) has been used as an alternative. However, due to concerns of various factors, including costs, efficiency, and animal welfare, there is a need for devices and methods that replace animal uses altogether.

SUMMARY OF THE INVENTION

This invention relates to devices for evaluating the sensitization potential of one or more known or novel chemical entities, or a combination thereof, thereby identifying chemicals or other agents that cause skin sensitization.

Accordingly, one aspect of this invention features a device having a tubular wall defining a chamber. The chamber has, among others, a region that is in fluid communication with one or more input channels and an outlet, and a face that is suitable for mounting a skin tissue and in fluid communication with the region. The chamber and the region are capable of being filled with and holding a fluid. The region can be in a shape of a semicircle or others. The outlet can include a plurality of weirs defining a plurality of channels that allow a flow of a liquid while blocking a cell, such as an antigen presenting cell (APC) or a T cell. An example of the device is shown in FIGS. 1A-D.

The invention also features a system for evaluating skin sensitizing activity of a test compound. The system has a plurality of the devices mentioned above and a housing for holding the plurality of devices while exposing at least a portion of the face of each chamber. The housing is suitable for mounting a skin tissue. The above mentioned microfabricated chamber and system can be used in evaluating skin sensitizing activity.

In a second aspect, the invention features a method for evaluating skin sensitizing activity of a test compound. The method includes steps of (i) contacting a skin tissue with a test compound for a first period of time, (ii) contacting the skin tissue with a plurality of antigen presenting cells (APCs) for a second period of time, (iii) mixing the APCs with a plurality of T cells, and (iv) measuring the level of activation of the T cells. The level of the activation is indicative of the skin sensitizing activity of the test compound. The level of activation can be preformed by various ways known in the art, e.g., examining an intra- or extracellular marker. Examples of the marker include CD25, CD125, CD134, CD69, CD62L, CD44, CD45 and CD95. The APCs can contain dendritic cells or Langerhans cells. In one embodiment, the skin tissue is mounted on the device disclosed above. In another, the method is conduced in a high throughput manner using a plurality of the devices or the system of this invention. The high throughput method and device allow one to evaluate the sensitization potential of a large number (e.g., 5, 10, 20, 50, 100, 200, 300, 400, 500, or 1000) of agents in parallel at the same time.

In other aspects, the invention provides use of the devices or systems for determining skin-sensitizing or non-sensitizing property of a agent or a plurality of agents in parallel, determining a prognosis of sensitization in a subject, and determining whether a subject has a risk of developing a disease or disorder associated with inflammation in response to an agent or a plurality of agents in parallel.

The details of one or more embodiments of the invention are set forth in the description below. Other features, objects, and advantages of the invention will be apparent from the description and from the claims.

BRIEF DESCRIPTION OF THE DRAWINGS

FIGS. 1A, 1B, 1C, 1D and 1E are photographs showing top views (A-C) and a side view (D) of an exemplary device having a microfabricated chamber with details of two areas shown (B and C). FIG. 1E shows an individual device and a housing holding a plurality of devices.

DETAILED DESCRIPTION OF THE INVENTION

Figure 1E:
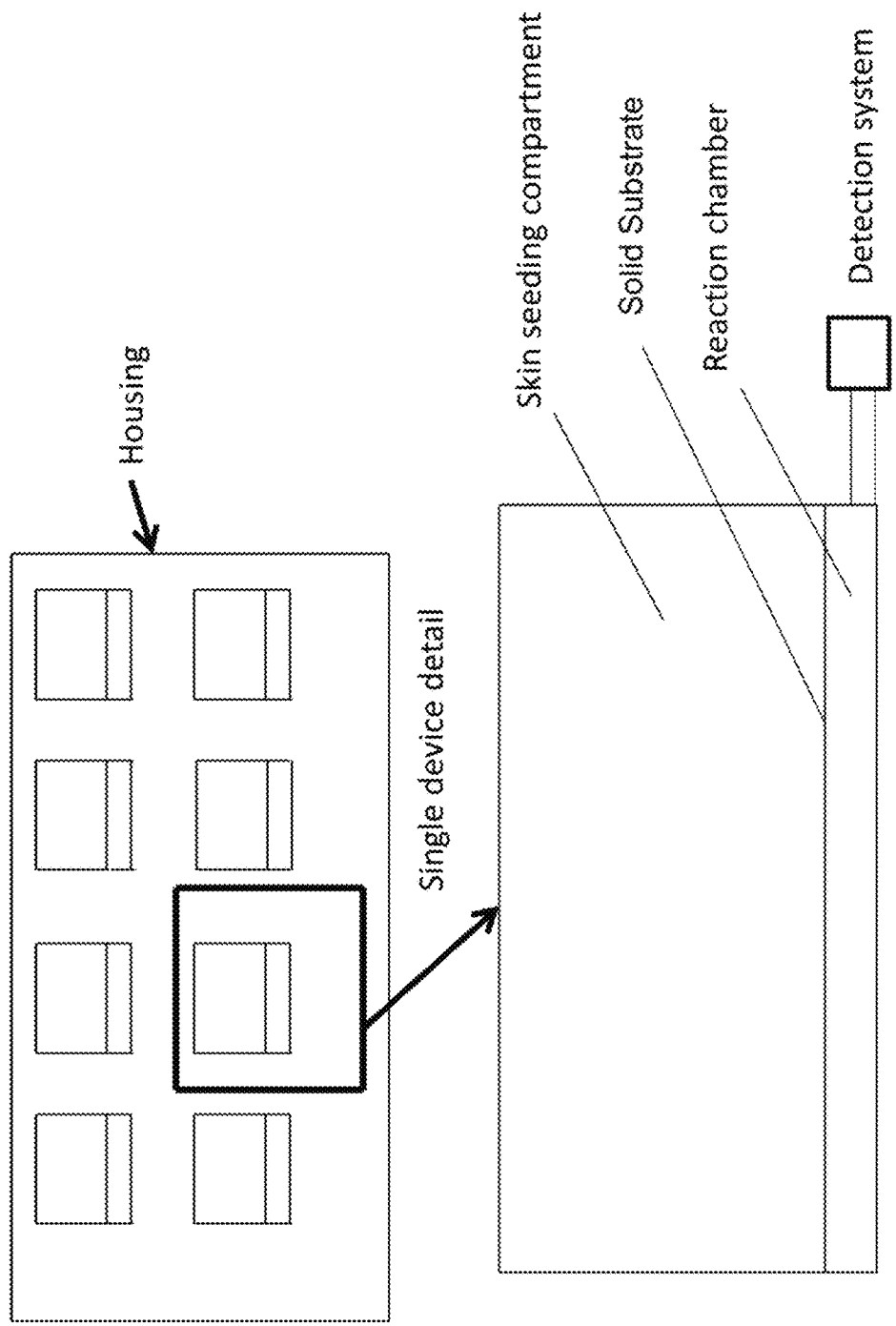

This invention is based, at least in part, on unexpected discoveries that the in vivo skin sensitization response can be recapitulated in vitro using the device as disclosed herein.

In one embodiment, the device includes one or more microfabricated chambers in which antigen presenting cells (APCs) such as Langerhans cells and/or dendritic cells are co-cultured with a skin tissue. A chemical can be applied topically on top of the skin. Chemicals that act as sensitizers can induce maturation of APCs, which can activate T cells. T cells can be introduced into the microfabricated chamber where they are activated by the mature APCs. The activation of T cells provides the end point assay for detecting the sensitization potential of a chemical.

Shown in FIGS. 1A-D is an exemplary device of this invention. The device has a semicircular region connected by input channels for introducing APCs and T cells ("APC Seeding Channel" and "T-Cell Seeding Channel"). The outlet of the semicircular region consists of multiple weirs that allows for the flow of liquid while blocking APCs and T cells within the circular region. The top of the chamber is such that the skin can be mounted. The top contains multiple holes through which intercellular communication between the APCs and the skin can occur.

The T cell activation can be evaluated in a number of ways including but not limited to the secreted factor(s) and the expression of both intra and extracellular marker(s) on T cells. The invention can be used to exploit all the key cellular elements that participate in the localized lymph node assay (LLNA) conducted in vivo for determining the sensitization potency of a chemical. The microfabricated chamber facilitates experiments that require small volume of reagents and number of cells per condition further promoting high throughput experiments in parallel.

For example, for measuring the T cell activation, intra and extracellular markers on T cells can be estimated via microscopic imaging within the chamber. For measuring secreted factor(s), additional microfabricated modules can be integrated with the chamber for assaying the soluble factor(s) in the medium.

Currently there is a need to move away from animal testing for cosmetics in Europe, and potentially in the US. The device described herein is able to predict the sensitization potential of a new chemical entity, or combination of entities by recapitulating the in vivo sensitization response.
Devices The device of this invention has a rapid reaction, microfluidics chamber, where T-cells, peripheral cells, and dendritic cells are brought together with the sensitizer. The secretome can be then moved into a detection system, which can be a rapid sandwich immunoassay on a chip, capable of multi-plex detection of numerous secreted proteins capable, which when analyzed with either on-chip detection, or off-chip high throughput flow cytometer, can detect the degree of sensitization.

The technology is novel and much quicker in terms of generating data. Furthermore it is more user-friendly then currently applied sensitization-assessment techniques, and is more amenable to scale-up.

The device and microfluidics chambers described above have a solid substrate. The solid substrate can be a material that may be modified to contain discrete individual sites appropriate for the attachment of a skin tissue or cells and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing. The substrate can be planar, although other configurations of substrates may be used as well.
Cells Antigen presenting cells (APCs) are a group of cells that are important to elicit an effective immune response. APCs not only present antigens to T cells with antigen-specific receptors, but also provide the signals necessary for T cell activation. Such signals involve a variety of cell surface molecules, as well as the production of cytokines and/or growth factors. The signals necessary for the activation of naive or unprimed T cells are believed to be different from those required for the re-activation of previously primed memory T cells.

APCs include monocytes, B cells, and dendritic cells. Monocytes and B cells have been shown to be competent APCs although their antigen presenting capacities appear to be limited to the re-activation of previously sensitized T cells. These cell types are not capable of directly activating functionally naive or unprimed T cell populations. On the other hand, dendritic cells are capable of both activating naive and previously primed T cells. Dendritic cells are a heterogeneous cell population with a distinctive morphology and a widespread tissue distribution, including blood. (See, e.g. Steinman, Ann. Rev. Immunol. 9:271-96 (1991).) The cell surface of dendritic cells is unusual, with characteristic veil-like projections. Mature dendritic cells are generally identified as $CD11c^+HLA-DR^+$, $CD86^+$, $CD54^+$, $CD3^-$, $CD19^-$, $CD14^-$, $CD11c^+$ and $HLA-DR^+$.

APC-depleted T cells can be prepared from which co-stimulatory signal has been removed. Co-stimulatory signals can be removed, for example, by "panning" using antibodies against MHC class II molecules. For example, T cells or PBMC can be contacted with magnetic beads coupled to antibodies specific for MHC class II molecules to remove co-stimulatory signal. As used herein, T cell substantially free of co-stimulatory signal generally exhibit an insignificant level of T cell activation (e.g., less than about 5%, or less than about 1%, of the activity of fully activated T cells).

APCs can be prepared from a variety of sources, including human and non-human primates, other mammals, and vertebrates. In certain embodiments, APCs can be prepared from blood of a human or non-human vertebrate. APCs can also be isolated from an enriched population of leukocytes. Populations of leukocytes can be prepared by methods known to those skilled in the art. Such methods typically include collecting heparinized blood, apheresis or leukopheresis, preparation of buffy coats, resetting, centrifugation, density gradient centrifugation (e.g., using Ficoll (such as FICOLL-PAQUE), PERCOLL™ (colloidal silica particles), sucrose, and the like), differential lysis of non-leukocyte cells, filtration, and the like. A leukocyte population can also be prepared by collecting blood from a subject, defibrinating to remove the platelets and lysing the red blood cells. The leukocyte population can optionally be enriched for monocytic dendritic cell precursors.

Blood cell populations can be obtained from a variety of subjects, according to the desired use of the enriched population of leukocytes. The subject can be a healthy subject. Alternatively, blood cells can be obtained from a subject in need of immunostimulation, such as, for example, a cancer patient or other patient for which immunostimulation will be beneficial. Likewise, blood cells can be obtained from a subject in need of immune suppression, such as, for example, a patient having an autoimmune disorder (e.g., rheumatoid arthritis, diabetes, lupus, multiple sclerosis, and the like). A population of leukocytes also can be obtained from an HLA-matched healthy individual.

In other embodiments, the dendritic cells can be isolated according to other methods known to the skilled artisan. See, e.g., OF'Doherty et al, J. Exp. Med. 178:1067-76 (1993); Young and Steinman, J. Exp. Med. 171:1315-32 (1990); Freudenthal and Steinman, Proc. Natl. Acad. Sci. USA 87:7698-702 (1990); Macatonia et al., Immunol 67:285-89 (1989); Markowicz and Engleman, J. Clin. Invest. 85:955-

61 (1990); U.S. Pat. Nos. 5,994,126 and 5,851,756. The disclosures of these documents are incorporated by reference herein. Methods for immuno-selecting dendritic cells include, for example, using antibodies to cell surface markers associated with dendritic cell precursors, such as anti-CD34 and/or anti-CD14 antibodies coupled to a substrate (see, e.g., Bernhard et al., Cancer Res. 55:1099-104 (1995); Caux et al., Nature 360:258-61 (1992)) or associated with fully differentiated dendritic cells, such as, CD11c, CD54, CD83, CD80, CD86, and the like.

T cells for use according to the present invention can be prepared according to methods known in the art. The T cells can be an enriched T cell preparation, an APC-depleted T cell preparation, or a substantially purified T cell preparation. T cells, or a subset of T cells, can be obtained from various lymphoid tissues. Such tissues include, but are not limited to, the spleen, lymph nodes, and peripheral blood. The T cells can be a mixed T cell population or a purified T cell subset.

In certain embodiments, the T cells are an enriched T cell preparation, in which the number or percentage of T cells is increased with respect to an isolated population of T cells. In other embodiments, the T cells are substantially free of APCs, in which most (e.g., >75%) of the APCs have been separated from the T cells. In an exemplary embodiment, peripheral blood mononuclear cells (PBMCs) can be obtained from blood, such as in heparinized vials. The PBMCs can be separated from red blood cells by centrifugation (e.g., using HISTOPAQUE® 1077 (Sigma Aldrich Co.)) and PBMCs recovered from the interface. The recovered PBMCs optionally can be washed (e.g., with PBS).

T cell purification can be achieved, for example, by positive or negative selection including, but not limited to, the use of antibodies directed to CD2, CD3, CD4, CD5, CD8, CD14, CD19, and/or MHC class II molecules. The T cell preparations useful in the present invention are typically $CD4^+$ or a mixed population of $CD4^+$ and $CD8^+$. In certain embodiments, T cell preparations contain at least about 50% T cells. In additional embodiments, the T cells can be an isolated T cell line.

Screening Methods

The above-describe devices or related kits can be used in determining whether a compound tends to cause sensitization. Alternatively, they can be used for determining a prognosis of sensitization in a subject. Accordingly, this invention provides screening methods for identifying a compound that does not cause sensitization. The compound thus-identified can be used to in a cosmetic composition. Such a compound can be identified according to the methods described below.

In one embodiment, the method of this invention includes the steps of providing T cells having a known functional activity and being substantially free of co-stimulatory activity and providing a sample of APCs of unknown co-stimulatory activity. The APCs are contacted with a skin tissue that has been contacted to a test compound. The T cells are contacted with a sample of APCs. Subsequently the activation of the T cells contacted with the APCs is determined and compared to a standard activation level for the T cells to determine the activity of the APCs. The qualitative or quantitative amount of a predetermined antigen taken up by the cells, processed and/or presented can also be determined. Typically, antigen uptake, processing and/or presentation is determined by, for example, Western blotting, flow cytometry, or activation of antigen-specific T cells.

The T cells used in the methods of the present invention can either be syngeneic or allogeneic with the APCs or the skin tissue. Typically, the T cells used in the methods of the invention are isolated from peripheral blood mononuclear cells. The T cells can have T cells from a sample of peripheral blood mononuclear cells depleted of cells expressing MHC class II, CD14, CD54, CD80, CD83, and/or CD86 molecules on their surface.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify the above-mentioned compound, one can contact a candidate compound with a skin tissue mounted on the device described. One then measures activation levels of the T cells.

T cell activation can be determined during and/or following co-culturing of the T cells and the APCs. Suitable assays for T cell activation include DNA replication assays (e.g., $^3$H-thymidine incorporation), extracellular and/or cytokine production assays (e.g., ELISA, flow cytometry, and the like), and T cell activation marker assays (e.g., flow cytometry).

Activation of T cells can be correlated with T cell proliferation, such as DNA replication, which can be measured, for example, by labeled thymidine incorporation (e.g., $^3$H-thymidine or other suitable label). Co-cultures of T cells and APCs can be pulsed with the label (e.g., $^3$H-thymidine, about 1 µCi/device) for about 6 to about 24 hours. The cells can then be collected (e.g., using a cell harvester) and the incorporated radioactivity measured by liquid scintillation spectroscopy. In certain embodiments, the APCs can be inactivated prior to co-culturing with the T cells to prevent APC DNA replication. Alternatively, the T cells can be separated from the APCs prior to determining the amount of label incorporated.

T cell activation also can be measured by extracellular or intracellular cytokine production, such as, for, example, IFNγ and/or IL-2 production, and the like. Extracellular cytokine production can be measured by determining changes in levels of one or more cytokines in culture media. Typically an immunoassay (e.g., ELISA assay, sandwich assay, immunoprecipitation assay, or Western blotting) can be used, although other assays can also be suitable. (See, e.g., Harlow and Lane, Using Antibodies, A Laboratory Manual, Cold Spring Harbor Laboratory, New York (1999), the disclosure of which is incorporated by reference herein.) For intracellular cytokine levels, immunoassays or other assays can be used. The T cells can optionally be separated from the APCs (e.g., by collection based on expression of T cell markers), prior to assay for intracellular cytokine levels. (See, e.g., Harlow and Lane, supra).

In additional embodiments, T cell activation can be determined by modulation of T cell activation markers. Such markers include, for example, CD25 (also referred to as Interleukin 2 receptor alpha chain), CD69 (also referred to as VEA or AIM), CD44 (also referred to as Pgp-1), CD125 (also referred to as IL-2 receptor beta chain), and the like. The modulation of T cell activation markers can be measured, for example, by determining changes in protein levels or mRNA levels. For example, changes in protein levels can be determined by flow cytometry using labeled antibodies against the T cell activation markers, transcription factors or other proteins associated with T cell activation, by immunoassay, such as, ELISA or Western blotting, and the like. Changes in mRNA levels can be determined for the message encoding the T cell activation markers, transcription factors, and the like. mRNA levels can be determined by, for example, Northern blotting, polymerase chain reaction (e.g., RT-PCR), other hybridization assays (e.g., assays using GeneChip™ probe arrays, and the like), or other assays. (See, e.g., Sambrook et al., Molecular Cloning, A Laboratory Manual, 3rd ed., Cold Spring Harbor Publish., Cold Spring Harbor, N.Y. (2001); Ausubel et al., Current Protocols in Molecular Biology, 4th ed., John Wiley and Sons, New York (1999); U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference.)

Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

The presence, level, or absence of the nucleic acid or polypeptide in a test sample can be evaluated by obtaining a test sample and contacting the test sample with a compound or an agent capable of detecting the polypeptide or nucleic acid (e.g., mRNA or genomic DNA probe). The "test sample" includes tissues, cells and biological fluids. The level of expression of a gene(s) of interest can be measured in a number of ways, including measuring the mRNA encoded by the gene; measuring the amount of polypeptide encoded by the gene; or measuring the activity of polypeptide encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Alternatively, RNA is isolated using solid-phase oligo-dT capture using oligo-dT bound to microbeads or cellulose columns. This method has the added advantage of isolating mRNA from genomic DNA and total RNA, and allowing transfer of the mRNA-capture medium directly into the reverse transcriptase reaction. Other RNA isolation methods are contemplated, such as extraction with silica-coated beads or guanidinium. Further methods for RNA isolation and preparation can be devised by one skilled in the art.

The methods of the present invention can also be performed using crude cell lysates, eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products. For example, one of the two target-specific primers could be designed to span a splice junction, thus excluding DNA as a template. As another example, the two target-specific primers can be designed to flank a splice junction, generating larger PCR products for DNA or unspliced mRNA templates as compared to processed mRNA templates. One skilled in the art could design a variety of specialized priming applications that would facilitate use of crude extracts as samples for the purposes of this invention.

The level of mRNA corresponding to a gene in a cell can be determined both in situ and in vitros. Messenger RNA isolated from a test sample can be used in hybridization or amplification assays that include, Southern or Northern analyses, PCR analyses, and probe arrays. A preferred method for the detection of mRNA levels involves contacting the isolated mRNA with a nucleic acid probe that can hybridize to the mRNA encoded by the gene. The probe can be a full-length nucleic acid or a portion thereof, such as an oligonucleotide of at least 10 nucleotides in length and sufficient to specifically hybridize under stringent conditions to the mRNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for detecting the level of an mRNA.

The level of mRNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to mRNA. Alternative methods for amplifying nucleic acids corresponding to expressed RNA samples include those described in, e.g., U.S. Pat. No. 7,897,750.

In another embodiment, the methods of the invention further include contacting a control sample with a compound or agent capable of detecting the mRNA of a gene and comparing the presence of the mRNA in the control sample with the presence of the RNA in the test sample.

The above-described nucleic acid-based methods can provide qualitative and quantitative information to determine whether a compound tends to cause sensitization.

A variety of methods can be used to determine the level of the polypeptide encoded by a gene. In general, these methods include contacting an agent that selectively binds to the polypeptide, such as an antibody, to evaluate the level of polypeptide in a sample. Antibodies can be polyclonal, or more preferably, monoclonal. An intact antibody, or a fragment thereof (e.g., Fab or F(ab')$_2$) can also be used. In a preferred embodiment, the antibody bears a detectable label. The term "label" refers to a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}I$, $^{131}I$, $^{35}S$, $^{3}H$, or $^{32}P$), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles by the Quantum Dot Corporation, Palo Alto, Calif.).

The detection methods can be used to detect a polypeptide in a biological sample. In vitro techniques for detection of the polypeptide include ELISAs, immunoprecipitations, immunofluorescence, EIA, RIA, and Western blotting analysis.

The methods described herein can also be used to identify whether a subject has a risk of developing a disease or disorder associated with inflammation in response to an agent. The prognostic assays can be used to determine whether a subject is suitable to be administered with an agent (e.g., an agonist, antagonist, peptidomimetic, protein, peptide, nucleic acid, small molecule, or other drug candidate) to treat a disorder without causing skin sensitization or inflammation.

Information obtained from practice of the above assays is useful in prognostication, identifying progression of, and clinical management of diseases and other deleterious conditions affecting an individual's health status. In preferred embodiments, the foregoing diagnostic assays provide information useful in prognostication, identifying progression of and management of conditions that are characterized by inflammation. The information more specifically assists the clinician in designing treatment regimes to eradicate such conditions from the body of an afflicted subject, a human.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

A "test sample" or a "biological sample" as used herein may mean a sample of biological tissue or fluid that comprises nucleic acids. Such samples include, but are not limited to, tissue (e.g., a skin tissue) isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Examples

Device Design

For illustration purpose, FIGS. 1A-D show an exemplary device of this invention, which contains a reaction chamber. The device has a semicircular region connected by input channels for introducing APCs and T cells ("APC Seeding Channel" and "T-Cell Seeding Channel"). The outlet of the semicircular region consists of multiple weirs that allows for the flow of liquid while blocking APCs and T cells within the circular region. The top of the chamber is such that the skin can be mounted. The top contains multiple holes through which intercellular communication between the APCs and the skin can occur.

Figure 2:
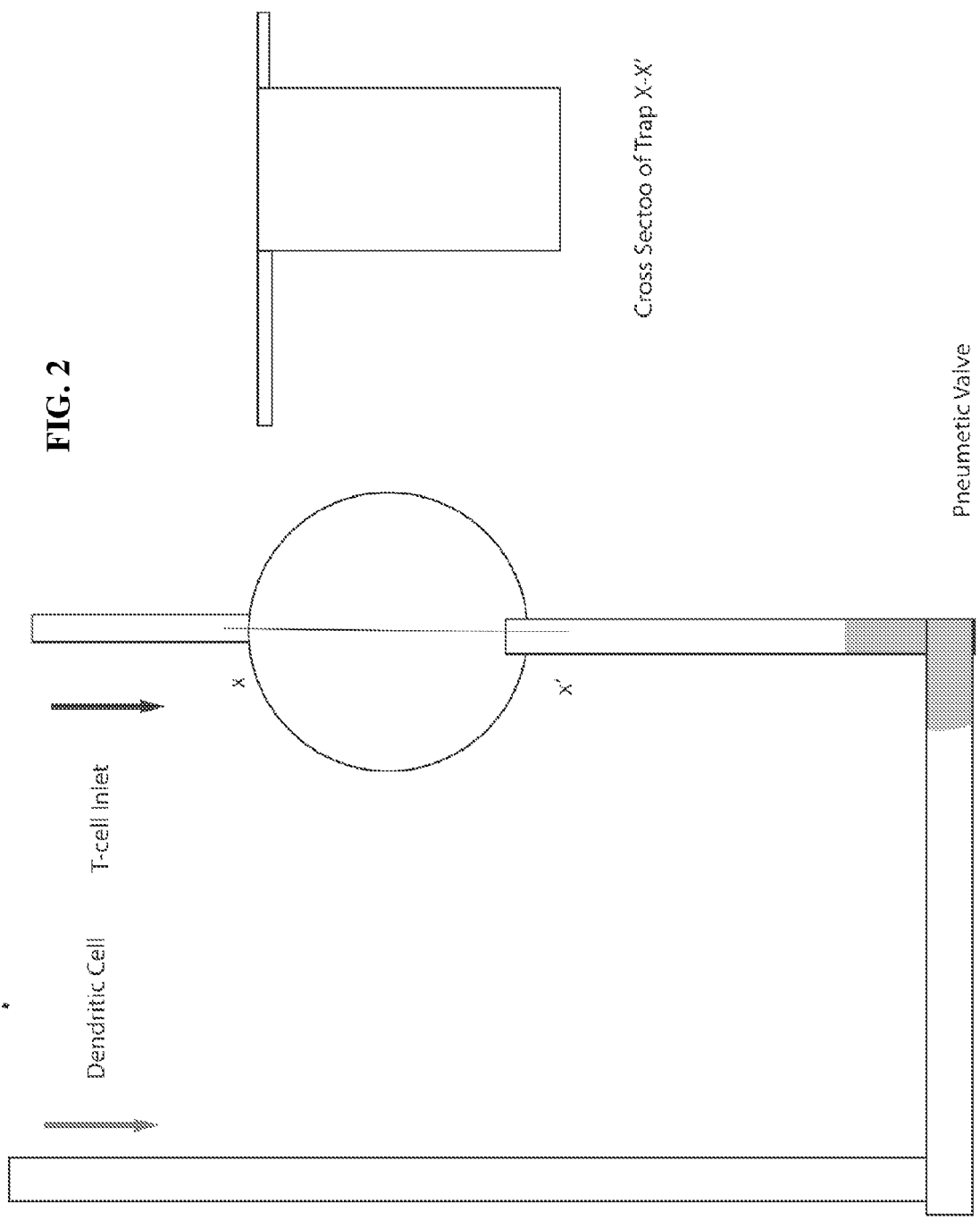
FIG. 2 illustrates a basic setup of the device. The device reaction chamber contains a microfluidic well-trap. As cells pass through the well, they sink to the bottom, causing them to be trapped. The advantage of this topology is that it prevents clogging which happens in other kinds of traps.

FIG. 2 illustrates the basic setup of the reaction chamber. A well-trap (150 um deep and 500 um diameter) is utilized to trap the cells as they pass through the fluidic channel. Trapping cells in microfluidic channels is a deceptively complex problem. The general principle is to have some sort of a limiting filter which traps the cells, but not the media. However, such devices tend to clog up easily with debris, and once filled, show a dramatic increase in fluidic resistance, which makes it difficult to introduce cells of different types into the chamber. Further, it makes the integration of the cell trap with other microfludic structures (e.g., chemeotaxis chamber on the upstream, or on chip ELISA on the downstream) extremely difficult.

With a well-trap these problems are readily avoided. As cells pass through the well, they sink to the bottom, causing them to be trapped. Debris, which is of light weight, floats at the top and is removed. Since there is a minimal change in fluidic resistance in the flow path, the device is easy to be integrated into larger systems.

The device is mounted on to an acrylic manifold, which is aligned such that a set screw is aligned on top of the microfluidic channel. Turning the screw causes it to press down on the microfluidic channel, causing it to fully or partially close.

The device is fabricated in PDMS by replica molding a Master made of SU8. Other materials may be employed—this particular material was utilized since it's permeable to oxygen, and easy to rapid prototype.

Experimental Method

T cells are isolated from the peripheral blood mononuclear fraction by positive selection using CD3 microbeads and magnetic cell separator (Miltenyi Biotec Inc., Auburn, Calif.), following the manufacturer's instructions. The T cells are frozen in liquid nitrogen and thawed prior to use. The T-cells are labeled with a calcium sensitive fluorescent dye, Fluo-4. The present method measures the increase in calcium flux into T-cells, as they form immunological synapses with dendritic cells. For labeling, the T cells are suspended at a density of $1-2\times10^6$ cells/ml in the medium supplemented with the fluo4 dye diluted to a final concentration of 1 µM. The cells are incubated at 37° C. for 20 minutes, and then washed twice to remove the remaining dye in the medium. The labeled T cells are suspended in the fresh medium prior to loading in the microdevice.

The device is first primed with PBS. Any bubbles, remaining from the priming process, are removed by placing the device in a vacuum dessicater for 1-2 minutes. Once primed, the device is flushed with media. Dendritic cells (DCs) are introduced into the device from inlet 1, by means of a 2.5 µL pipette. Additional head is provided by topping off the pipette tip attached to the device to the required level. The set-screw valves may be employed to adjust the flow to allow the cells to slow down enough so they can settle.

Figure 3:
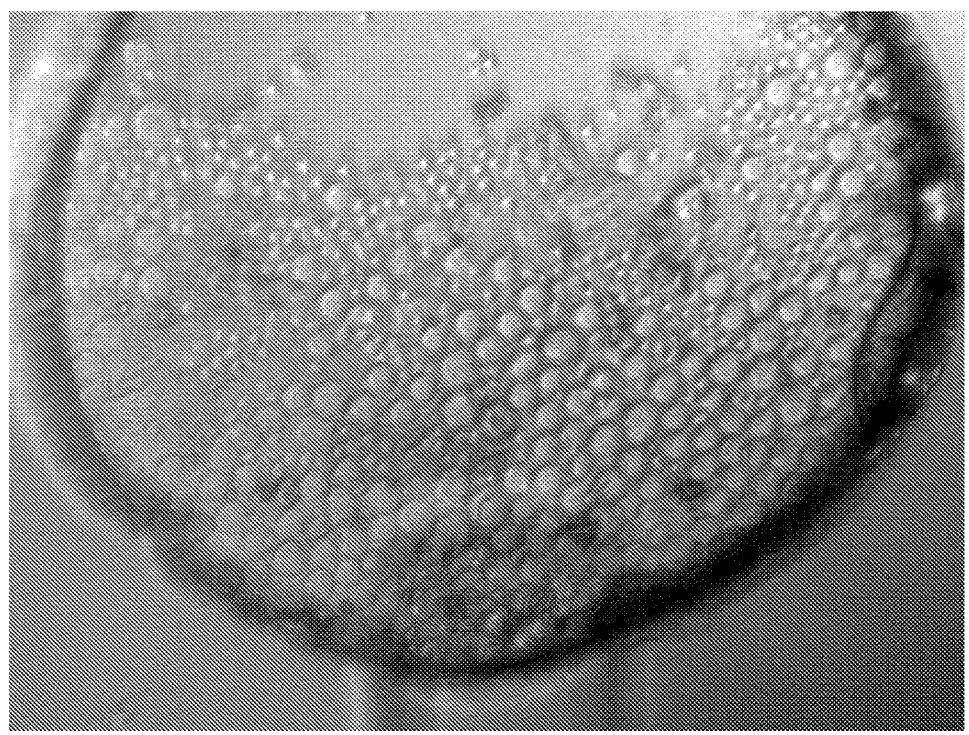
FIG. 3 shows a typical loading at the bottom of the chamber. The dendritic cells and T-cells are trapped at the bottom of the well trap.

Once the DCs are loaded, the outlet is cleaned and flushed to remove any cells that might have gone across. Subsequently, T-cells are introduced from the outlet side. FIG. 3 shows a typical loading at the bottom of the chamber. Once sufficient number of T-cells have accumulated, the valve is closed and the system is placed under a microscope for imaging, and time lapse microscopy is performed.

Results

Figure 4:
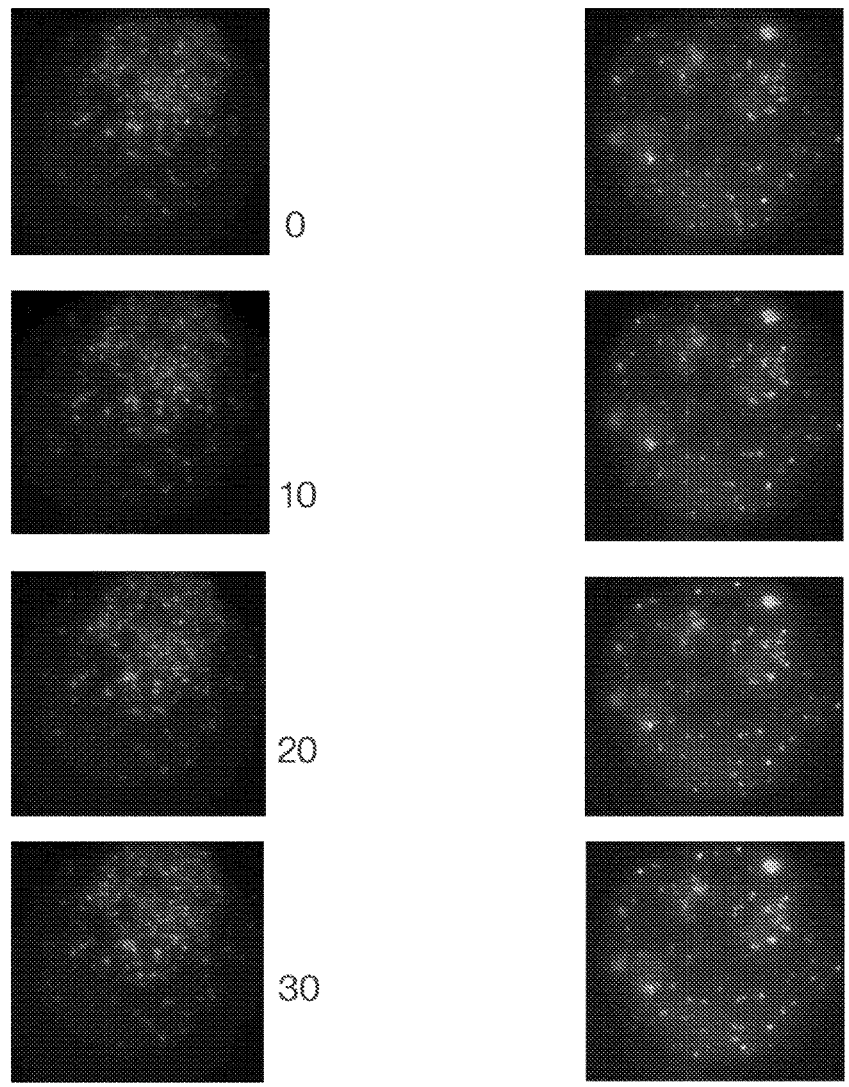
FIG. 4 shows time lapse microscopy of mature and immature cells in the device, which illustrates the evolution of fluorescence over time: (left) Immature Dendritic Cells, and (right) Mature dendritic cells.
Figure 5:
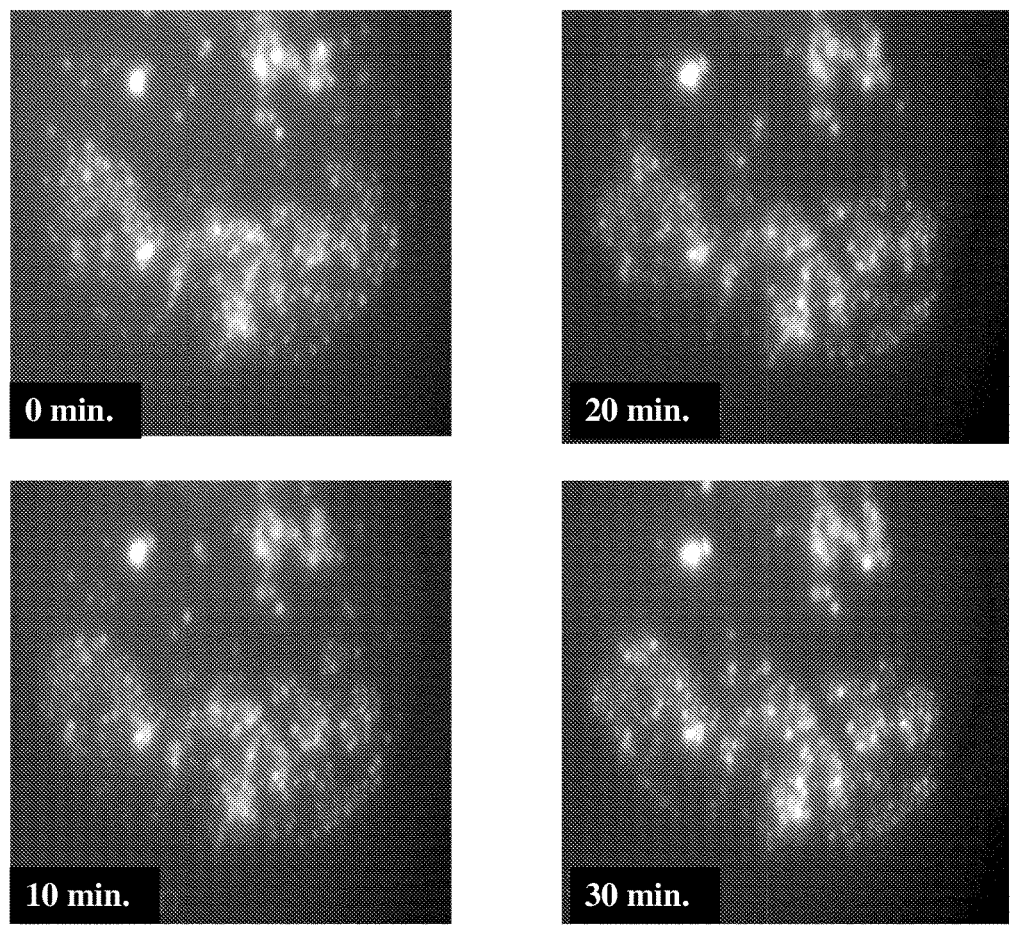
FIG. 5 shows results of a similar experiment, with cells sensitized with PPD. The Mutz DCs are sensitized with PPD with T-cells in the chamber. Sensitized Mutz show similar response to mature dendritic cells.

The reaction chamber can be employed in myriad ways. For example, one may just let the cells interact and observe changes in cell morphology, agglomeration, or proliferation. FIG. 4 shows time lapse microscopy of mature and immature cells in the device. In mature cells, the T-cells arrange themselves in clusters around the dendritic cells. With time, the size and the fluorescence activity of the clusters are seen to increase. Correspondingly, such an increase is not seen in immature cells. FIG. 5 shows a similar experiment, with cells sensitized with PPD. Clustering accompanied by increase in fluorescence is observed.

The foregoing description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. A device comprising a tubular wall defining a chamber, the chamber comprising:
    a region comprising (i) a solid substrate for attachment of cells, (ii) one or more input channels and (iii) an outlet, and
    a face that is suitable for mounting a skin tissue and is in fluid communication with the region,
    wherein the chamber and the region are capable of being filled with and holding a fluid, and the outlet comprises a plurality of weirs defining a plurality of channels that allow a flow of a liquid while blocking a cell.

2. The device of claim 1, wherein the region further comprises a microfluidic well trap capable of trapping cells when they pass through the well trap.

3. The device of claim 1, the substrate comprising discrete individual sites suitable for attachment of a skin tissue or cells and being amenable to at least one detection method.

4. The device of claim 3, wherein the substrate is made from a material selected from the group consisting of glasses, plastics, polysaccharides, nylons, nitrocellulose, resins, carbon, metals, silica, and silica-based materials.

5. The device of claim 4, wherein the glasses are selected from inorganic glasses, modified glasses, and functionalized glasses; wherein the plastics are selected from acrylics, polystyrene, copolymers of styrene and other monomers, polypropylene, polyethylene, polybutylene, polyurethanes, and TeflonJ; and wherein said silica-based materials are selected from silicon and modified silicon.

6. The device of claim 3, wherein the substrate allows optical detection without fluorescence.

7. The device of claim 3, wherein the substrate is planar.

8. The device of claim 1, wherein the region is semicircular.

9. The device of claim 8, wherein the semicircular region is connected by input channels for introducing APCs ("APC Seeding Channel") and T cells ("T-cell Seeding Channel").

10. The device of claim 1, wherein the cell is selected from antigen presenting cells (APCs) or T cells.

11. The device of claim 1, wherein the device is coupled with a detection system that comprises a rapid sandwich immunoassay on a chip, capable of multiplex analysis of secreted proteins.

12. The device of claim 11, wherein said analysis is conducted with an on-chip or off-chip high throughput flow cytometer.

13. A system for high throughput analysis of agents for their skin-sensitizing or non-sensitizing properties, the system comprising:
    a plurality of the devices according to claim 1, and
    a housing for holding the plurality of devices while exposing at least a portion of the face of each chamber.

14. The system of claim 13, wherein the housing is suitable for mounting a skin tissue.

15. A method for evaluating skin-sensitizing activity of a test compound, comprising:
contacting a skin tissue with a test compound for a first period of time; wherein the skin tissue is mounted on the device of claim 1;
contacting the skin tissue with a plurality of antigen presenting cells (APCs) for a second period of time;
mixing the APCs with a plurality of T cells; and
measuring the level of activation of the T cells,
whereby the level of the activation is indicative of the skin sensitizing activity of the test compound.

16. The method of claim 15, wherein the level of activation is preformed by examining an intra- or extra-cellular marker.

17. The method of claim 15, wherein the marker is selected from the group consisting of CD25, CD125, CD134, CD69, CD62L, CD44, CD45 and CD95.

18. The method of claim 15, wherein the APCs comprise cells selected from dendritic cells and Langerhans cells.

19. The method of claim 15, wherein the APCs are generated from mammals or vertebrates.

20. The method of claim 15, wherein the APCs are generated from humans or non-human primates.

21. The method of claim 15, wherein the APCs are isolated from a population of leukocytes.

22. The method of claim 15, wherein the leukocyte population is enriched with monocyclic dendritic cell precursors.

23. The method of claim 15, wherein the T cells are an enriched T cell preparation, an APC-depleted T cell preparation, or a substantially purified T cell preparation.

24. The method of claim 15, wherein the T cells are obtained from lymphoid tissues selected from spleen, lymph nodes, and peripheral blood.

25. The method of claim 15, wherein the T cells are a mixed T cell population or a purified T cell subset.

26. The method of claim 15, wherein the T cells are an enriched T cell preparation, in which the number or percentage of T cells is increased with respect to an isolated population of T cells.

27. The method of claim 15, wherein more than 75% of the APCs have been separated from the T cells.

28. The method of claim 15, wherein the T cells are substantially free of APCs.

29. The method of claim 15, wherein the peripheral blood mononuclear cells (PBMCs) are obtained from blood.

30. The method of claim 15 conducted in a high throughput manner using a plurality of said device in parallel.

31. The method of claim 30 conducted in high throughput manner using a housing for holding the plurality of devices while exposing at least a portion of the face of each chamber.

32. The method of claim 15, wherein the test compound is selected from proteins, peptides, peptidomimetics, peptoids, antibodies, and small molecules.

33. The method of claim 15, further comprising contacting a control sample with a compound or agent capable of detecting the mRNA of a gene and comparing the presence of the mRNA in the control sample with the presence of the mRNA in the test sample, whereby the higher level of the mRNA in the test sample is indicative of sensitization capability of the test sample.

34. A method for evaluating skin-sensitizing activity of a test compound, comprising the steps of:
(a) providing T cells having a known functional activity and being substantially free of co-stimulatory activity;
(b) providing a sample of APCs of unknown co-stimulatory activity;
(c) contacting the APCs with a skin tissue that has been contacted to a test compound; wherein the skin tissue is mounted on the device of claim 1;
(d) contacting the T cells with a sample of APCs;
(e) determining activation level of the T cells contacted with the APCs; and
(f) comparing the activation level of the T cells contacted with the APCs to a standard activation level for the T cells to determine the activity of the APCs;
whereby the activity of the APCs is an indication of skin-sensitizing activity of the test compound.

35. The method of claim 34, further comprising determining the amount of antigen taken up by the T cells.

36. The method of claim 35, wherein the antigen uptake is determined by Western blotting, flow cytometry, or activation of antigen-specific T cells.

37. A kit for detecting skin-sensitivity of agents comprising a device according to claim 1, and written instructions of use.

* * * * *